US006497916B1

(12) United States Patent
Taylor et al.

(10) Patent No.: US 6,497,916 B1
(45) Date of Patent: Dec. 24, 2002

(54) COATING

(75) Inventors: Alistair Stewart Taylor, Surrey (GB); Lee Alan Tollhurst, Surrey (GB); Donal Thomas Hempensall, Uxbridge (GB)

(73) Assignee: Biocompatibles Limited, Surrey (GB)

( * ) Notice: Subject to any disclaimer, the term of this patent is extended or adjusted under 35 U.S.C. 154(b) by 0 days.

(21) Appl. No.: 09/693,837

(22) Filed: Oct. 23, 2000

Related U.S. Application Data

(62) Division of application No. 09/357,987, filed on Jul. 21, 1999, now Pat. No. 6,214,115.

(30) Foreign Application Priority Data

Jul. 21, 1998 (EP) ........................................... 98305788

(51) Int. Cl.[7] ......................... A61L 27/00; A61L 27/28; B05D 7/16; B05D 7/22; B05D 1/18

(52) U.S. Cl. .................... 427/2.24; 427/2.25; 427/2.28; 427/2.3; 427/230; 427/238; 427/294; 427/295; 427/429; 427/435

(58) Field of Search ............................... 427/2.24, 2.25, 427/2.28, 2.3, 230, 238, 294, 295, 429, 435

(56) References Cited

U.S. PATENT DOCUMENTS

| | | | | | |
|---|---|---|---|---|---|
| 976,715 | A | | 11/1910 | Willner | 118/50 |
| 2,050,830 | A | | 8/1936 | Delany | 118/423 |
| 3,109,751 | A | | 11/1963 | Audet et al. | 118/423 |
| 3,661,621 | A | * | 5/1972 | Jager | 117/68 |
| 5,045,353 | A | * | 9/1991 | Takada et al. | 427/243 |
| 5,067,654 | A | | 11/1991 | Paige | 239/124 |
| 5,332,437 | A | | 7/1994 | Davene et al. | 118/423 |
| 5,833,651 | A | * | 11/1998 | Donovan et al. | 604/53 |
| 6,153,252 | A | * | 11/2000 | Hossainy et al. | 427/2.3 |
| 6,156,373 | A | * | 12/2000 | Zhong et al. | 427/2.28 |
| 6,203,732 | B1 | * | 3/2001 | Clubb et al. | 164/464 |

* cited by examiner

*Primary Examiner*—Shrive P. Beck
*Assistant Examiner*—Jennifer Kolb Michener
(74) *Attorney, Agent, or Firm*—Sughrue Mion, PLLC

(57) ABSTRACT

An apparatus for coating tubular members, such as stents comprises a liquid reservoir and a stent support member for supporting, in use, a tubular member. Support member dipping means places the support member in the liquid reservoir in use and draws the support member therefrom. Pressure differential generating means generates a pressure differential. The stent support member is arranged to provide a central passageway through a stent placed thereon, the central passageway having a plurality of perforations formed therein, and the pressure differential generating means is arranged to generate, in use, a pressure differential between the passageway and the tubular member.

8 Claims, 6 Drawing Sheets

COATING

This is a divisional of application Ser. No. 09/357,987 filed Jul. 21, 1999 now U.S. Pat. No. 6,214,115, the disclosure of which is incorporated herein by reference.

This invention relates to the coating of tubular members, such as stents.

During the manufacture of stents it is often necessary to coat a stent with a liquid. The liquid may be a biocompatible material or a coating which encases the stent with a material once the liquid has dried. Such coating has often been performed by manually dipping the stent in the liquid and then removing the stent and drying it. Such a process leads to manufacturing inconsistency. Furthermore, many stents have plural apertures formed in the surface thereof and the presence of excess liquid or inconsistent drying of the liquid can lead to such apertures becoming blocked unnecessarily.

The present invention seeks to overcome the above and other problems.

According to the present invention there is provided an apparatus for coating tubular members, such as stents, the apparatus comprising:

- a liquid reservoir;
- a stent support member for supporting, in use, a tubular member;
- support member dipping means for placing the support member in the liquid reservoir in use and drawing the support member therefrom; and
- pressure differential generating means for generating a pressure differential, wherein:
  - the stent support member is arranged to provide a central passageway through a stent placed thereon, the central passageway having a plurality of perforations formed therein, and
  - the pressure differential generating means is arranged to generate, in use, a pressure differential between the passageway and the tubular member.

The support member may be formed from a rigid hollow member, such as a needle, with apertures formed therein. The support member may alternatively be formed from a rigid member having a series of slots formed therein. With such an arrangement a sheath may be placed around the external periphery of the member to define a series of circular perforations. The support member may be formed from metal, a plastics material, or a combination thereof.

The pressure differential generating means may be a pump. The support member may have two collars and a central rigid support member, the collars arranged to engage with each end of a tubular member in use.

The dipping means may be arranged to enable inversion of the support member once it has been removed from the liquid reservoir.

The apparatus may further comprise a drying chamber into which a heated gas can be pumped to dry the tubular member on the support member after removal from the liquid reservoir.

Plural support members may be provided in the apparatus. Each support member may support plural stents.

A corresponding method is also provided.

The apparatus and method of the present invention provides a system which produces consistent coating results. Furthermore, because the pressure differential that is generated can prevent apertures becoming blocked with dried solution, stents with apertures that are produced by the apparatus and method are less likely to be rejected because of such blockages. In addition the apparatus and method can produce a thin coating (for example in the region 5 nm to 200 nm) on the inside of the stent whilst producing a thicker coating (for example 500 nm to 1500 nm) on the outside.

One example of the present invention will now be described with reference to the accompanying drawings, in which.

Figure 1:
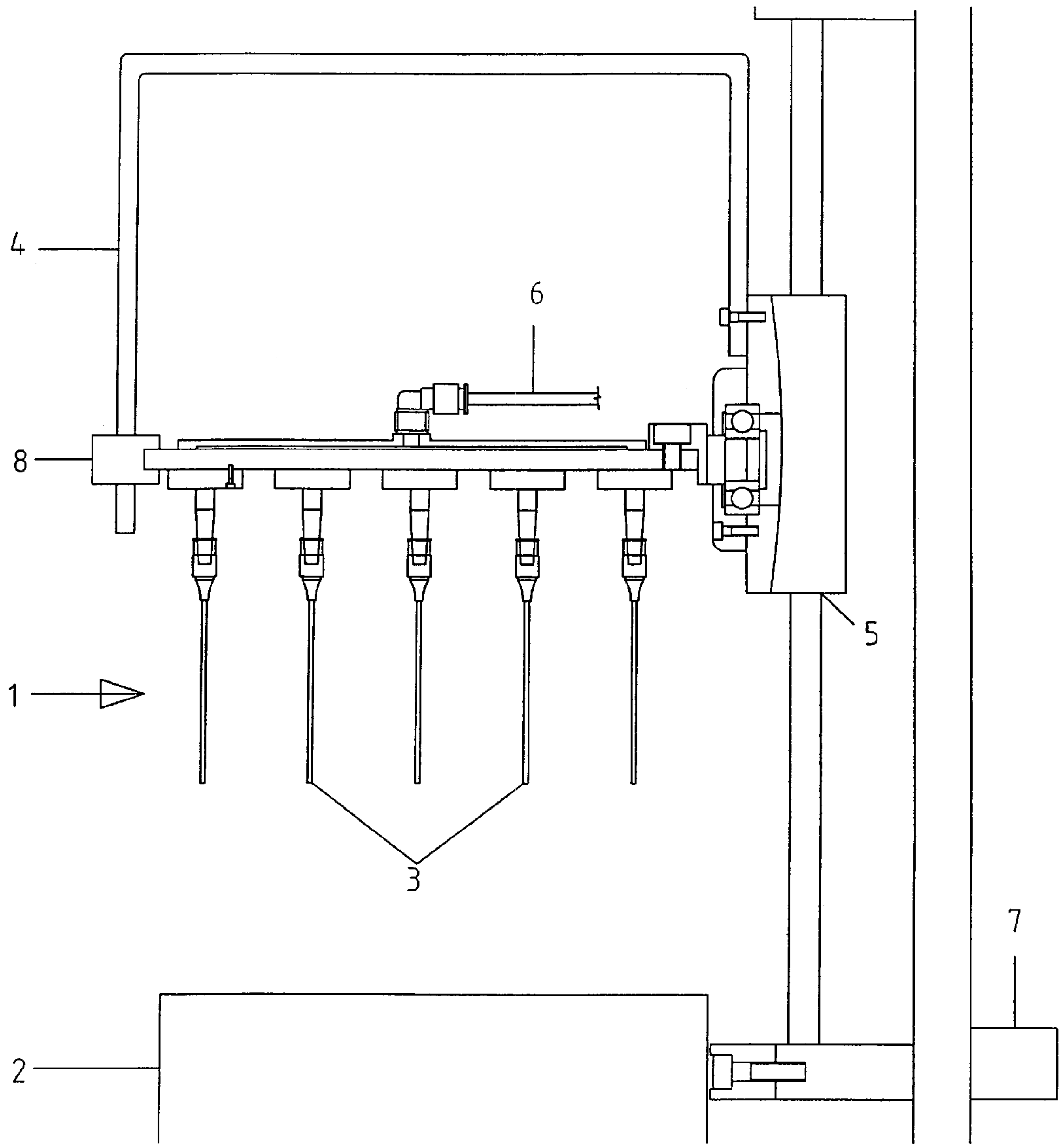
FIG. 1 is a side view of an apparatus according to the present invention.

Referring to FIG. 1, an apparatus 1 according to the present invention has a liquid reservoir 2 which, in use, holds a coating solution. Plural support members 3 are arranged in the form of an array on a frame 4 which is slidably supported on a support pillar 5. The frame 4 can be driven up and down on a support pillar 5 by a servo motor and drive mechanism (not shown).

Each of the support members 3 is formed from a hollow tube, with the interior of each tube being connected to a conduit 6 which, in turn, is connected to a vacuum pump 7. The frame 4 supporting the support members 3 is arranged so that it can be rotated around a central axis 8 under the control of an operator or servo motor (not shown). Rotation of the frame 4 allows rotation of the support members 3 from a position in which they are directed generally downwards to a position in which they are directed generally upwards.

The apparatus 1 is operated by placing the stent on each support member 3 and retaining the stent thereon. The stent may be retained by the provision of one or more collars (not shown) attached to each support member 3, the collars arranged to prevent the stent moving to any significant degree along the axis of the support member during the coating process. The frame is then rotated so that the unattached end of each of the support members 3 is pointing downward. Once this has been done the frame 4 is lowered into the liquid reservoir 2 and then drawn up from the liquid reservoir 2 at a rate which ensures even coating. The rate will generally be determined by the dimensions of the stents being coated and the viscosity of the liquid contained within the liquid reservoir 2.

Once the frame 4 and support members have been removed from liquid in the liquid reservoir 2 the frame 4 is rotated through 180° so that each of the support members is pointing in a generally upward direction. A pressure differential is then created by the vacuum pump 7 so that air is drawn through apertures 9 in each of the support members via conduit 6 to the vacuum pump 7. The airflow generated by the pressure differential ensures that liquid is not retained in any of the apertures of the stents. The pressure differential may be generated whilst the frame 4, support members 3 and stents are contained within a drying chamber (not shown).

Figure 2:
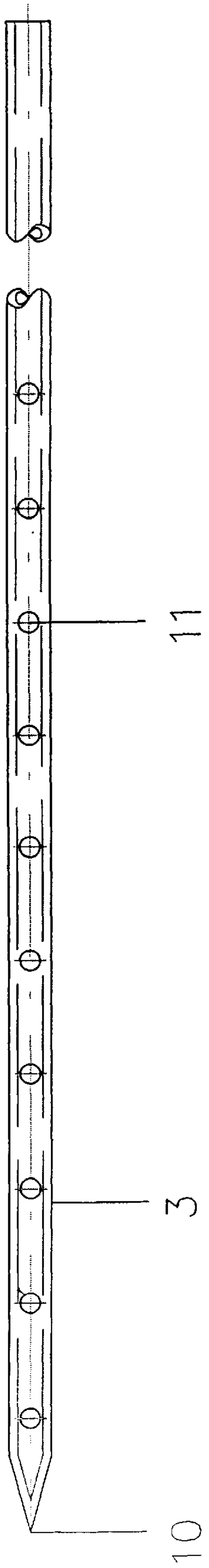
FIG. 2 is a side view of a first example support member for use in the apparatus of FIG. 1.
Figure 3:
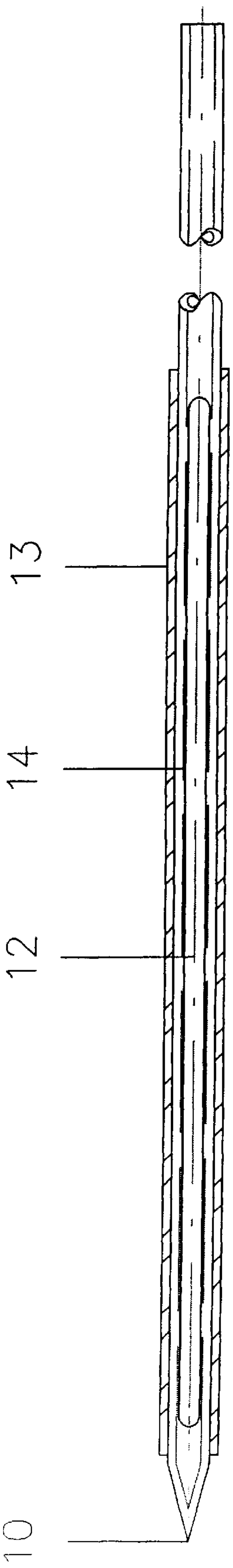
FIG. 3 is a side cross-sectional view of a second example support member for use in the apparatus of FIG. 1.
Figure 4:
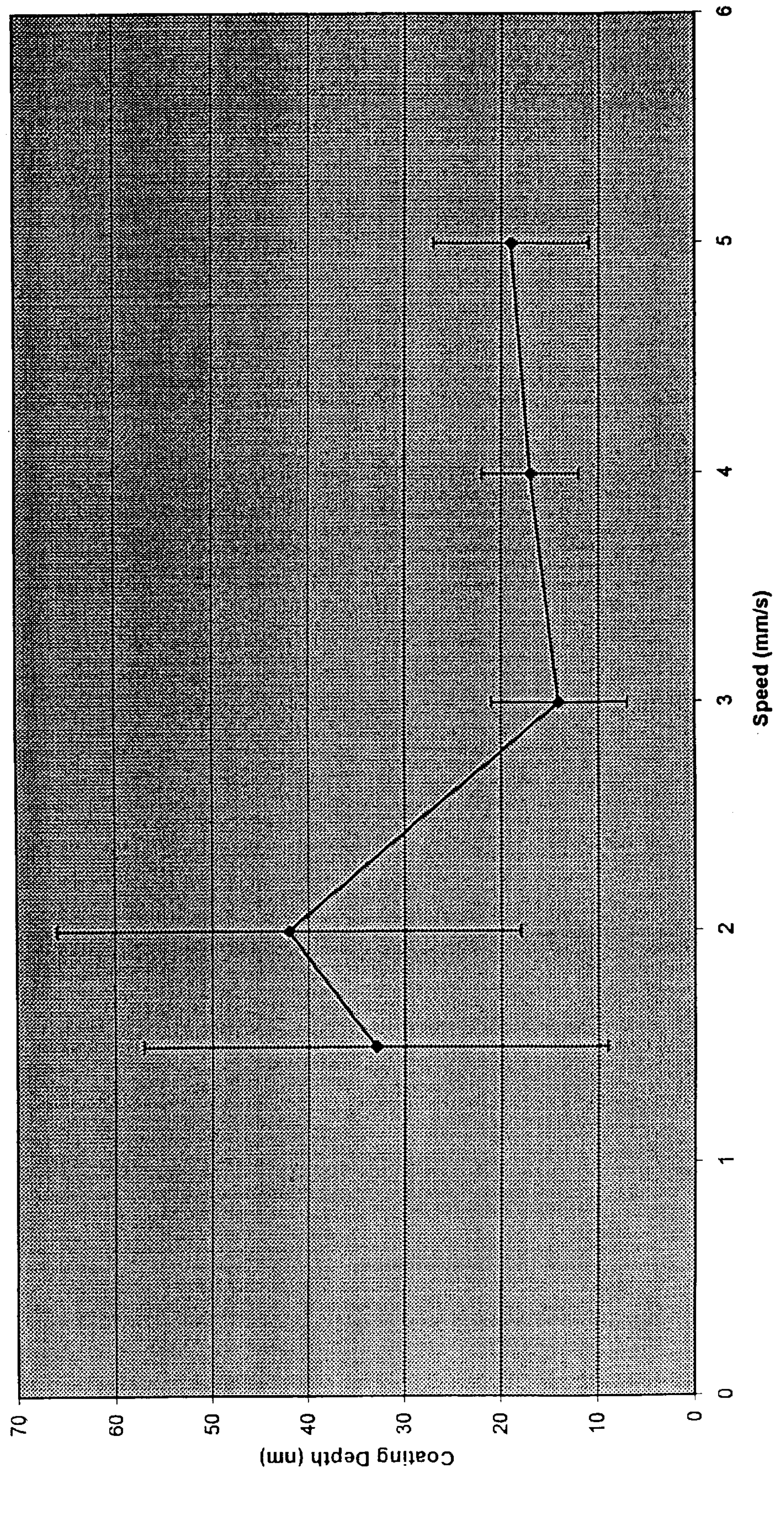
FIG. 4 is a graph of coating depth versus withdraw speed for the outer surface of an exemplary stent.
Figure 5:
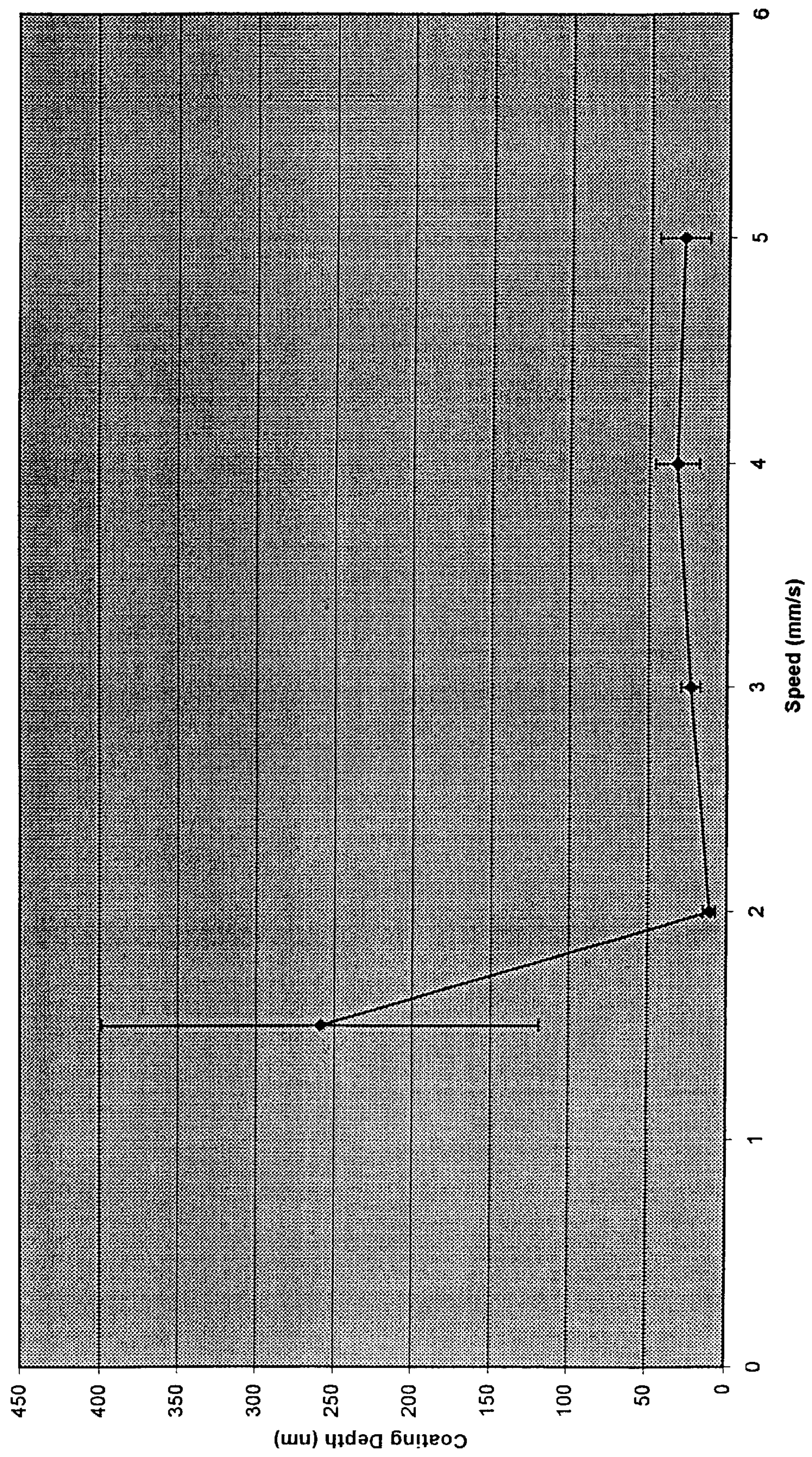
FIG. 5 is a graph of coating depth versus withdraw speed for the inner surface of an exemplary stent.
Figure 6:
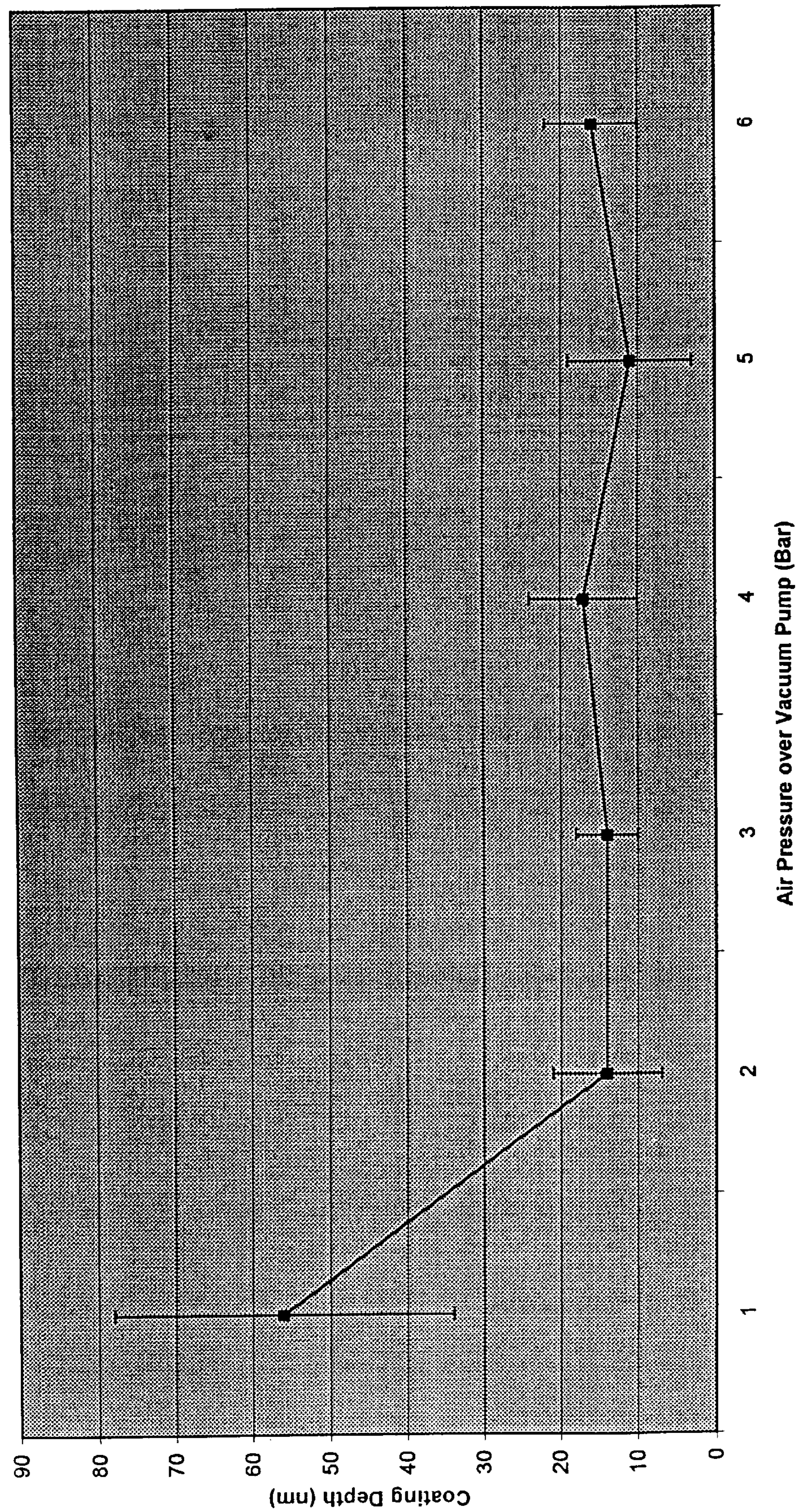
FIG. 6 is a graph of coating depth versus pressure differential from the outer surface of an exemplary stent.
Figure 7:
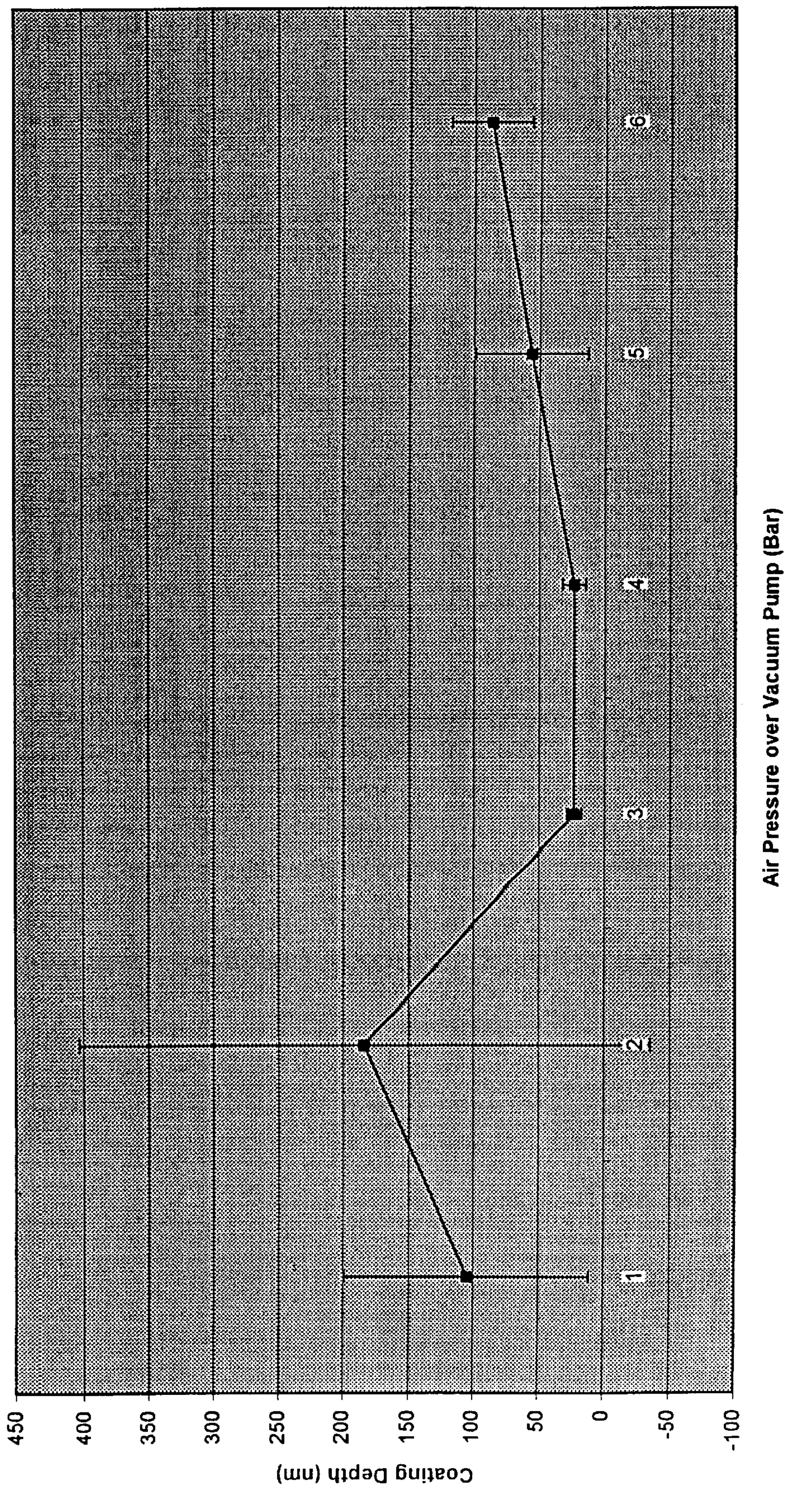
FIG. 7 is a graph of coating depth versus pressure differential for the inner surface of an exemplary stent.

FIGS. 2 and 3 show example support members 3 which can be employed in the apparatus 1 of FIG. 1.

The support member 3 of FIG. 2 is formed from a hollow tube with a sealed end 10, the member 3 being formed from stainless steel or any other sufficiently rigid material. Formed on the surface of the member 3 are a series of apertures 11, which allow passage of air from the exterior of the member 3 through to its hollow interior. The support member 3 may be attached by a quick release mechanism to the apparatus 1.

FIG. 3 shows an alternative support member 3 in which the support member 3 is formed from a rigid hollow tube having one or more slots 12 formed in a surface and parallel to its axis. A sheath 13, formed from a plastics material, ceramic, or other appropriate material is placed around the external periphery of the support member 3. The sheath 13 has a plurality of apertures 14, or may have one or more spiral slots formed around its outer surface. This arrangement also defines apertures through which air can be drawn in use.

Referring to FIGS. 4 to 7, it can be seen that the speed of withdraw of the stent and support member 3 from liquid reservoir 2 can control both the outer and inner coating depth so that an optimum coating depth can be provided. Furthermore, by appropriate control of the value of the pressure differential generated by the vacuum pump 7, further control of inner and outer coating depths can be provided. Control of withdraw speed and pressure differential may be effected by provision of apparatus control means (not shown) which can be configured easily by an operator dependent upon the type of tubular member that is being coated.

What is claimed is:

1. A method for coating an apertured tubular medical member with a liquid, the method comprising the steps of:

providing the liquid in a liquid reservoir;

supporting the tubular member on a support member, said support member having a passageway;

placing the support member, with the tubular medical member thereon, in the liquid reservoir and drawing the support member and tubular medical member therefrom at a rate which controls the thickness of the coating; and generating a pressure differential between the passageway of the support member and the tubular member to ensure that the liquid is not retained in any apertures of the tubular medical member.

2. The method of claim 1, further comprising the step of drying the member in heated gas.

3. The method of claim 1, further comprising the step of inverting the tubular member prior to generating the pressure differential.

4. The method of claim 1, wherein the rate at which the support member is drawn and the pressure differential is controlled to produce a coating that is thinner on the inside surface of the tubular member than it is on the outside.

5. The method of claim 2, further comprising the step of inverting the tubular member prior to generating the pressure differential.

6. The method of claim 2, wherein the rate at which the support member is drawn and the pressure differential is controlled to produce a coating that is thinner on the inside surface of the tubular member than it is on the outside.

7. The method of claim 3, wherein the rate at which the support member is drawn and the pressure differential is controlled to produce a coating that is thinner on the inside surface of the tubular member than it is on the outside.

8. A method of claim 1, wherein the tubular member is a stent.

* * * * *